(12) United States Patent
Strecker

(10) Patent No.: US 6,645,241 B1
(45) Date of Patent: *Nov. 11, 2003

(54) ENDOPROSTHESIS THAT CAN BE PERCUTANEOUSLY IMPLANTED IN THE PATIENT'S BODY

(76) Inventor: Ernst Peter Strecker, Vierordstrasse 7a, D-7500 Karlsruhe (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/776,850

(22) Filed: Feb. 6, 2001

Related U.S. Application Data

(63) Continuation of application No. 08/707,820, filed on Sep. 4, 1996, now Pat. No. 6,193,746, which is a continuation of application No. 08/393,950, filed on Feb. 22, 1995, now abandoned, which is a continuation of application No. 08/087,520, filed on Jul. 2, 1993, now abandoned.

(30) Foreign Application Priority Data

Jul. 8, 1992 (DE) .......................................... 42 22 380

(51) Int. Cl.[7] .................................................. A61F 2/06
(52) U.S. Cl. ...................................... 623/1.13; 623/1.42
(58) Field of Search ............................. 623/1.13, 1.14, 623/1.38–1.4, 1.42–1.43

(56) References Cited

U.S. PATENT DOCUMENTS

| | | |
|---|---|---|
| 3,279,996 A | 10/1966 | Long et al. |
| 3,426,758 A | 2/1969 | Harautuneian |
| 3,699,956 A | 10/1972 | Kitrilakis et al. |

(List continued on next page.)

FOREIGN PATENT DOCUMENTS

| | | |
|---|---|---|
| DE | 380 205 | 1/1924 |
| DE | 1196327 | 7/1965 |
| DE | OS 2 941281 | 3/1982 |
| DE | 39 18 736 A1 | 12/1990 |
| DE | 36 40 745 C2 | 3/1992 |
| EP | 0 166 998 B1 | 1/1986 |
| EP | 0 183 372 | 6/1986 |
| EP | 0 292 587 A1 | 11/1988 |
| EP | 306690 | 3/1989 |
| EP | 0 372 088 A1 | 6/1990 |
| EP | 0 379 156 A2 | 7/1990 |
| EP | 0 292 587 B1 | 11/1990 |
| EP | 0 399 712 A1 | 11/1990 |
| GB | 2112646 | 7/1983 |
| JP | 53/006430 | 1/1978 |
| SU | 1069826 | 1/1984 |
| WO | WO 89/12478 | 12/1989 |
| WO | WO 90/13332 | 11/1990 |
| WO | WO 91/08790 | 6/1991 |
| WO | WO 91/12779 | 9/1991 |
| WO | WO 92/06734 | 4/1992 |

OTHER PUBLICATIONS

Claude et al., Radiology (1992) pp. 184:185–190, "Intraluminal Bypass of Abdominal Aortic Aneurism: Feasibility Study"; Feb. 1992.

The Andreas Gruentzig Cardiovascular Center News Letter (Spring 1990).

Oppenheim et al., Proceed. Intern Symp. Rel. Bioact. Mater., 15, No. 33,1988.

(List continued on next page.)

Primary Examiner—David H. Willse
(74) Attorney, Agent, or Firm—Kenyon & Kenyon

(57) ABSTRACT

An endoprosthesis is provided. In one embodiment the endoprosthesis may include an elongated hollow structure that may be deliverable into a body lumen of a patient for dwelling therein. This structure may be expandable and may have an initial state of decreased outer diameter during delivery relative to the outer diameter of the structure during dwelling. The endoprosthesis may also include a lining impregnated with a medication for delivery to the patient wherein the lining may be continuous and connected along the structure and expandable therewith. It may also be deformable under pressure associated with expansion of the hollow structure, such that the lining does not crack during expansion.

30 Claims, 2 Drawing Sheets

U.S. PATENT DOCUMENTS

| | | |
|---|---|---|
| 4,026,296 A | 5/1977 | Stoy et al. |
| 4,140,126 A | 2/1979 | Choudhury |
| 4,299,226 A | 11/1981 | Banka |
| 4,321,711 A | 3/1982 | Mano |
| 4,330,497 A | 5/1982 | Agdanowski |
| 4,364,392 A | 12/1982 | Strother et al. |
| 4,417,576 A | 11/1983 | Baran |
| 4,423,725 A | 1/1984 | Baran et al. |
| 4,448,195 A | 5/1984 | LeVeen et al. |
| 4,481,323 A | 11/1984 | Sterling |
| 4,515,593 A | 5/1985 | Norton |
| 4,589,873 A | 5/1986 | Schwartz et al. |
| 4,592,340 A | 6/1986 | Boyles |
| 4,603,152 A | 7/1986 | Laurin et al. |
| 4,693,243 A | 9/1987 | Buras |
| 4,714,460 A | 12/1987 | Calderon |
| 4,732,152 A | 3/1988 | Wallsten et al. |
| 4,769,013 A | 9/1988 | Lorenz et al. |
| 4,775,380 A | 10/1988 | Seedham et al. |
| 4,784,647 A | 11/1988 | Gross |
| 4,820,270 A | 4/1989 | Hardcastle et al. |
| 4,832,688 A | 5/1989 | Sagae et al. |
| 4,876,126 A | 10/1989 | Takemura et al. |
| 4,879,135 A | 11/1989 | Greco et al. |
| 4,909,258 A | 3/1990 | Kuntz et al. |
| 4,923,450 A | 5/1990 | Maeda et al. |
| 4,950,256 A | 8/1990 | Luther et al. |
| 4,983,166 A | 1/1991 | Yamawaki |
| 4,993,412 A | 2/1991 | Murphy-Chutorian |
| 4,994,033 A | 2/1991 | Shockey et al. |
| 5,021,044 A | 6/1991 | Sharkawy |
| 5,026,607 A | 6/1991 | Kiezulas |
| 5,041,100 A | 8/1991 | Rowland et al. |
| 5,047,045 A | 9/1991 | Arney et al. |
| 5,049,132 A | 9/1991 | Shaffer et al. |
| 5,059,211 A | 10/1991 | Stack et al. |
| 5,091,205 A | 2/1992 | Fan |
| 5,102,402 A | 4/1992 | Dror et al. |
| 5,120,322 A | 6/1992 | Davis et al. |
| 5,163,952 A | 11/1992 | Froix |
| 5,197,977 A | 3/1993 | Hoffman et al. |
| 5,232,444 A | 8/1993 | Just et al. |
| 5,234,456 A | 8/1993 | Silvistrini |
| 5,282,823 A | 2/1994 | Schwartz et al. |
| 5,282,847 A | 2/1994 | Trescony |
| 5,316,023 A | 5/1994 | Palmaz et al. |
| 5,383,928 A | 1/1995 | Scott et al. |
| 5,500,013 A | 3/1996 | Buscemi et al. |
| 5,628,784 A | 5/1997 | Strecker |

OTHER PUBLICATIONS

Wollinsky H. et al., "Local Introduction of Drugs into the Arterial Wall: A Percutaneous Catheter Technique", Journal of Interventional Cardiology, vol. 2, No. 4, 1989, pp. 219–228.

Chapman et al., "A Bioabsorbable Stent: Initial Experimental Results", *Circulation* (Supp III) 82:0283 (abstract) (Oct. 1990).

Guyton, et al., "Inhibition of Rat Arterial Smooth Muscle Cell Proliferation by Heparin: In Vivo Studies with Anticoagulant and Nonanticoagulant Heparin," *Cir. Res.* 46:625–634 (May 1980).

McMath et al., "Experimental Application of Bioprotective Materials to Injured Arterial Surfaces with Laser Balloon Angioplasty", *Circulation* (Supp III) 82:0282 (abstract) (Oct. 1990).

Thompson et al., "Heparin and Growth Control of Vascular Cells," *Ann. N.Y. Acad. Sci.* 556:255–267 (1989).

Tidd et al., "Comparison of Hydrophilic Polymer–Coated Latex, Uncoated Latex and PVC Indwelling Balloon Catheters in the Prevention of Urinary Infection," *J.Urol*, 48:285–291 (1976).

Waller, B.F. et al., "Vessel Wall Pathology after Angioplasty," Cardio, Aug. 1990, P. 57.

Waller et al., "Morphologic Observations Late After Coronary Balloon Angioplasty" Mechanism of Acute Injury and Relationship to Restenosis, *Radio*, 174:961–967 (Mar. 1990).

Langer, "Drug Delivery," IUPAC Meeting, Montreal, Canada (Jul. 12, 1990).

ENDOPROSTHESIS THAT CAN BE PERCUTANEOUSLY IMPLANTED IN THE PATIENT'S BODY

RELATED APPLICATIONS

This is a continuation of application Ser. No. 08/707,820, filed Sep. 4, 1996, now U.S. Pat. No. 6,193,746, which is a continuation of application Ser. No. 08/393,950, filed Feb. 22, 1995, now abandoned, which is a continuation of application Ser. No. 08/087,520, filed on Jul. 2, 1993, now abandoned.

The present invention concerns an endoprosthesis. It is in the form of an elongated hollow structure. The structure can be implanted percutaneously with a catheter in a blood vessel or other cavity of the body. Once correctly positioned it will expand from an initial state with a narrow lumen into a state with a lumen that is as wide as its placement will allow.

Percutaneously implanted endoprostheses with variable lumens are known. They are employed to open or expand narrow blood-vessel lumens. The lumens can be expanded by mechanically stretching them with a known balloon catheter. They can also be compressed prior to implantation and stretch out on their own subject to the resilience introduced by the compression.

One endoprosthesis is disclosed in European A.0 292 587. It is mounted on a balloon catheter and can be dilated and removed from the catheter and left in a blood vessel. It is a stent manufactured by knitting, crocheting, or some other process for producing netting from metal or plastic filament of satisfactory tissue compatibility. The individual meshes consist of loosely interconnected loops. The loops undergo plastic deformation as the balloon expands, and the expanded prosthesis will remain expanded.

Self-expanding stents are described for example in European A 0 183 372 and U.S. Pat. No. 4,732,152. Such a prosthesis is prior to implantation compressed to a reduced cross-section against the force of its own resilience. It is then implanted in the body of a patient. Once the prosthesis has been correctly positioned, the compression is discontinued and the prosthesis springs back to its original shape inside the vessel, where it remains secured.

The endoprosthesis described in European A 0 183 372 is compressed to a reduced cross-section for purposes of implantation and then, while compressed, advanced with what is called a pusher through a catheter that has already been inserted in a vessel until the prosthesis arrives at the correct position in the vessel. Thrusting the prosthesis through the catheter requires considerable force because of the powerful friction encountered.

The system described in U.S. Pat. No. 4,732,152 includes a woven and resilient endoprosthesis kept compressed by a double wrapper closed at the distal end. The wrapping is removed from the compressed prosthesis as a stocking is removed from a leg. The ensuing friction can be avoided by injecting liquid between the wrapper's two sheets. This approach, elegant at first glance, because of the way it reduces friction, is nevertheless very difficult.

The object of the present invention is accordingly to completely improve the initially described generic endoprosthesis, which can be implanted with a catheter and has a variable lumen. The improved prosthesis will provide communication with or between cavities in the body and maintain that communication permanently. It will also be therapeutically useful.

This object is attained in accordance with the invention in the endoprosthesis in the form of an elongated hollow structure that can be implanted percutaneously with a catheter in a blood vessel or other cavity of the body and once correctly positioned will expand from an initial state with a narrow lumen into a state with a lumen that is as wide as its placement will allow, by a lining of a wrapping material that deforms plastically without fissuring as it expands from the state with the narrow lumen to the state with the wide lumen and that is impregnated with at least one medication that will gradually and preferably at a uniform rate be released to the patient once the prosthesis is in place.

A vascular prosthesis comprising a porous flexible tube of plastic with an elastomeric coating bonded to its outer surface and with both components medicated is admittedly known from German OS 2 941 281. This prosthesis, however, can expand to only a limited extent, and the expanding coating has a considerable range of elasticity. A considerable force of restoration is accordingly exerted on the stent in the expanded state and can undesirably reduce the expansion situation.

The present invention on the other hand exploits a wrapping material that plastically deforms as it expands and accordingly exerts no restoration force on the stent, ensuring persistent expansion.

Furthermore, the medicated wrapping material ensures precisely sited treatment of vascular conditions. The prosthesis can also be employed as a splint for tumorous stenoses and tumorous obstructions in the bile tract for example if it is impregnated with cytostatics or antiproliferatives.

Another embodiment of the prosthesis is a stent that can be implanted percutaneously with a catheter in a blood vessel or other cavity of the body. Once correctly positioned, the stent will expand from an initial state with a narrow lumen into a state with a lumen that is as wide as its placement will allow. This embodiment has a wrinkled lining around the as yet unexpanded stent. The lining smoothes out as the stent expands from the state with the narrow lumen to the state with the wide lumen. The lining is also impregnated with at least one medication. The medication will gradually and preferably at a uniform rate be released to the patient once the prosthesis is in place.

This prosthesis can also be adapted individually to the cross-section of the blood vessel it is implanted in even though the wrapping material itself does not stretch. Adaptation to the particular cross-section is, rather, achieved by the unfolding of the folded wrapping and its smoothing out against the wall of the vessel as the stent expands.

The lining in one practical advanced version of the invention is against either the outer surface or the inner surface of the prosthesis or both. It turns out to be practical in another advanced version of the invention for the lining to rest against all supporting areas of the prosthesis instead of just having a layer that rests against the inner and outer surfaces. This approach provides additional stabilization for the prosthesis in place.

This feature can easily be achieved when in accordance with still another advanced version the lining impregnated with at least one medication is applied by introducing the hollow structure or stent that supports the prosthesis into a mold along with liquid wrapping material that subsequently solidifies elastic. The advantage is that the walls of the embedded prosthesis will be absolutely smooth.

An implant is admittedly known from German OS 3 503 126 with a medicated collagen coating on the surface of a tubular support or stent. This coating, however, expands to only a limited extent, and the medication is released non-linearly.

The lining in another advantageous advanced version of the present invention is applied to the hollow structure or stent that supports the prosthesis once it has expanded to approximately half its final size. This ensures that the prosthesis will be uniformly coated even at maximal expansion.

To ensure the maximal possible absorption of medication while retaining the desirable mechanical properties of the prosthesis, the lining can be a flexible tubular membrane or sleeve wrapped around the prosthesis and secured. It will be practical in this event to ensure that the flexible tubular membrane adheres to the inner surface and/or the outer surface of the prosthesis and folds back around its ends.

Another sensible advanced version is characterized in that medications in the lining are dissolved in the wrapping material or included in the form of beads. This embodiment can also have openings in the inner and/or outer component of the lining to release the medication through. The openings expand as the prosthesis expands to the state with the wider lumen to the extent that medications are released once the lining has expanded to the utmost.

It can be practical for there to be more or less openings in the wall of the lining next to the lumen than there are in the wall next to the inner surface of the vessel. The ratio can be exploited to prescribe the dosage of medication to the lumen or wall of the blood vessel.

The wrapping material can also to advantage be biodegradable as long as its breakdown products provoke no undesirable side effects. When the material is biodegradable, the medication will be released not by diffusing out of the vehicle but by escaping as the vehicle that the medication is dissolved in or that accommodates the beads that encapsulate the medication at its surface decomposes and by accordingly coming into contact with body fluids. Administration is accordingly dependent on the rate of biodegradability of the vehicle, which can be adjusted.

The lining can to advantage be made of polymers or compounds thereof It can in particular be made of poly-D, L-lactide or poly-D,L-lactide co-trimethylene carbonate. It can also be made of albumin cross-linked with glutaraldehyde. In this event the aldehyde, which is thrombogenic, is removed once the albumin is cross-linked. The lining can also be made of polyacrylic or compounds thereof.

Stents coated with polymer and impregnated with medication are admittedly already known, for example from R. C. Oppenheim et al, Proc. Int. Symp. Contr. Rel. Bioact. Mat. 15 (1988), pages 52 to 55. These coatings, however, which are applied by spraying a dispersion of acrylic onto the stent, are not biodegradable, and there are no means of expanding the crosssection of the prosthesis.

It has also been demonstrated that once the prosthesis is in place the lining with at least one medication will be permeable enough for any metabolites that occur to enter the blood circulation through the wall of the vessel and for oxygen or nutrients for example to diffuse out of the blood through the lining to the wall of the vessel.

The wall with the lining of wrapping material in another important embodiment is either perforated at many points or is a knitted, crocheted, or otherwise produced mesh.

Another advanced version is characterized by pores in the lining for the substances to diffuse through. It is practical for the diameter of the pores to be no longer than 0.5 $\mu$m to prevent smooth-muscle cells from escaping through them from the wall to the lumen of an artery. It is important in this event for all areas of the endoprosthesis, especially intersections in the mesh, to be covered by the lining. When the prosthesis is made of filament by knitting or otherwise producing a mesh, it is important to ensure that only the filament that constitutes the endoprosthesis, which is usually a metal vehicle, is completely wrapped. It is simple in this event to make the mesh as open as possible.

It can be of advantage for the lining to be of several layers, each impregnated with different medications. The layers of the lining can be made of materials that biodegrade at different rates. The inner layer in particular can biodegrade more rapidly than the outer layer.

It has also been demonstrated practical for the inner layer of the lining to be impregnated with antithrombotics and the outer with antiproliferatives and/or other medicational substances. If the inner layer biodegrades more rapidly than the outer layer, the risk of thrombosis that is present during the first days after implantation will be effectively counteracted. The antiproliferative action on the other hand must be maintained longer, at least seven weeks. This can be ensured by the slower rate of biodegradation on the part of the outer layer.

The outer layer of the lining, the layer impregnated with antiproliferatives and/or other medicinal substances, consists in another important embodiment of a short cuff at each end of the prosthesis. This measure takes advantage of the information obtained from animal testing that constrictions will form rather rapidly after implantation at the ends of a prosthesis with a waterproof or non-porous inner and outer lining component. This effect is of course due to thromboses and proliferation at the intima. The cuffs themselves can be provided with pores. Small pores ensure constant fluid exchange accompanied by diffusion. The pores at the ends of the prosthesis counteract proliferation.

The outer layer of the lining in another advanced version of the invention can be impregnated with cytostatics to keep tumorous stenoses open. The inner layer can be impregnated with rheologically beneficial substances in order for example to promote the flow of bile through a stent in the bile tract. This feature is particularly significant because for example bile-tract stenoses are frequently associated with secondary infections of the tracts that lead to lumps adhering to the stent and obstructing the lumen.

A final advanced version of the endoprosthesis in accordance with the invention is characterized by a lateral aperture that expands extensively in accordance with the expanding lumen. This measure will keep branching blood vessels open. If the prosthesis is woven from metal, the aperture can be produced by cutting through one of the filaments in a mesh prior to expansion. As the stent expands, accordingly, the aperture will become wide enough to allow blood to flow through the branch. An endoprosthesis with a lateral aperture can also be employed in a branching bile tract. It must of course be ensured during implantation that the prosthesis is positioned properly with respect to the branch.

One practical embodiment is characterized by at least one flexible medicating tube extending outward along a lining in the form of a tubular membrane. The tube is intended to provide constant medication inside the lining. The measure ensures long-term supply of medication to the wall of the vessel. Blood flow, however, in contrast to what are called spraying balloons, will be maintained, and the medication can be supplied at low pressure without the mechanical damage to the wall of the vessel that occurs at the state of the art.

The medicating tube in one practical advanced version can be attached to and detached from the lining. It can accordingly be extracted from the membrane upon termination of medication. Several medicating tubes can also be uniformly distributed around the lining. A group of openings in the lining can be associated with each medicating tube. This measure will allow the medication to be introduced more or less isotropically along the circumference and hence applied to the surrounding wall of the blood vessel at a radially uniform pressure. A lining in the form of a tubular membrane can have an outward-extending medicating tube that accommodates radioactive liquids. The wall of the vessel can accordingly be exposed to temporary radiation without risk to the other tissues.

The lumen of a hollow structure that supports the prosthesis and has netting or meshes, finally, can narrow to such an extent when axial tension is applied to the prosthesis that it can be intercepted in a catheter and removed with the catheter from the vessel. The prosthesis can accordingly be extracted from the vessel and from the patient's body.

BRIEF DESCRIPTION OF THE DRAWINGS

Embodiments of an endoprosthesis in accordance with the invention will now be specified with reference to the schematic drawing, wherein

FIG. 7 is a longitudinal section through an endoprosthesis implanted in a vessel with a coating in the form of a tubular membrane with outer walls provided with openings to administer mediation through.

DETAILED DESCRIPTION

Figure 1:
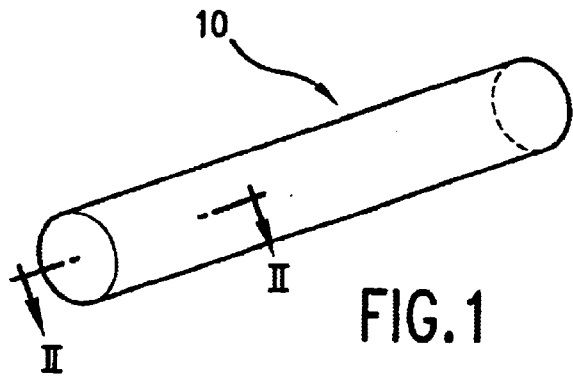
FIG. 1 illustrates an endoprosthesis in the form of an elongated hollow structure with a lining of medicated biodegradable wrapping material.
Figure 2:
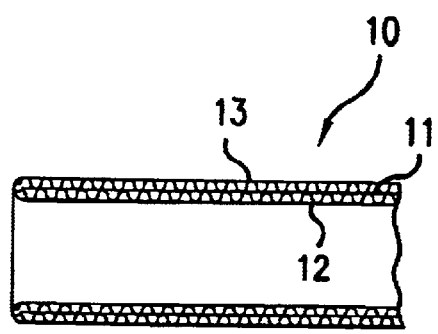
FIG. 2 is a larger-scale longitudinal section through the endoprosthesis along the line II—II in FIG. 1.

The endoprosthesis 10 illustrated in FIG. 1 is a tube with a variable lumen. Its wall 11 is completely enclosed in an inner lining component 12 and an outer lining component 13. The lining is applied by immersing the prosthesis in a liquid that subsequently solidifies. Medications are dissolved in the wrapping material. The material biodegrades without leaving deleterious decomposition products, while the medications gradually release.

Figure 3:
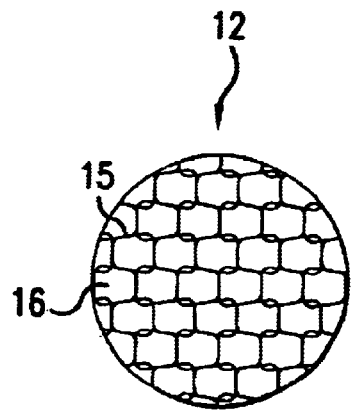
FIG. 3 is a section illustrating the structure of an endoprosthesis knitted out of metal filament and with meshes constituted of loosely interconnected loops.

FIG. 3 illustrates a section of the wall of the tube. The wall is knit from metal filament 15 into an open mesh of loosely engaged loops 16. There are particular advantages to this structure. It is flexible and elastic enough to follow the curvature of the vessel while being implanted. Once implanted it will be resilient enough to resist deformation from outside forces.

The thread itself in an endoprosthesis of the type illustrated in FIG. 3 can also be wrapped in a coat of medicated and biodegradable wrapping material. The wall of such a prosthesis is accordingly characterized by the presence of an open mesh. The prosthesis can of course alternatively be enclosed in a flexible-tubular coat.

Figure 4:
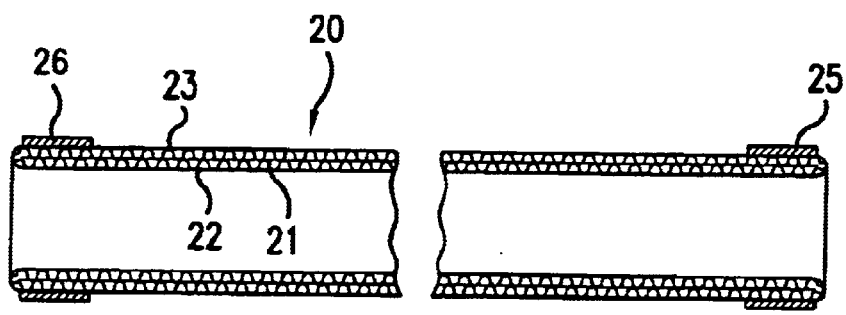
FIG. 4 is a view similar to that in FIG. 2 of an endoprosthesis with a multiple-layer lining and with its ends coated with medication.

The wall 21 of the endoprosthesis 20 illustrated in FIG. 4 has inner and outer layers 22 and 23 as well as multiple layer cuffs 25 and 26 of a biodegradable wrapping material at each end. Layers 22 and 23 of lining, which extend along the whole prosthesis, are impregnated with antithrombotics. Cuffs 25 and 26, which extend only slightly along it on the other hand, are impregnated with antiproliferatives to prevent any overgrowth of the ends due to thromboses or thromboarteritis as the prosthesis remains in place long term.

It can also be practical to impregnate only the ends of the type of prosthesis illustrated in FIG. 4 in order to ensure release of only a low dose and avoid systemic action. The endoprosthesis in accordance with the invention can for example concern a sterile metal stent. The stent is 4 cm long with an inside diameter of 4.0 mm. It is soaked in aseptic conditions in a solution of 4.00 g of poly-D,L-lactide (which has an inherent viscosity of 0.3), 0.35 g of triacetin, and 270 g of acetone. It is then allowed to dry (for 5 days at room temperature and for 16 days at a low pressure of 20 torrs) and at 40° C. at low pressure (4 days). The polymer coating (24 mg/cm) will now have a phase-transition temperature of 25+2° C. The polymeric solution can, however, also have 0.40 g of heparin suspended in it. The polymer coating will in this event comprise 2.0 mg/cm of heparin. The polymer coatings finally can be stored at 37° C. in an isotonic phosphate buffer with a pH of 7.4 at 37° C. In a test of this approach the polymer began to lose mass in 18 days and yielded a subsequent half time of 12 days. The molar mass-reduction half time was 10 days.

Figure 5:
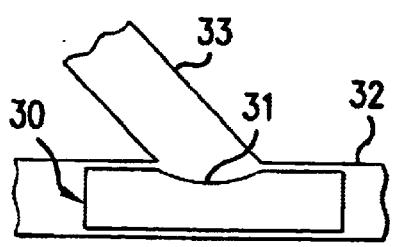
FIG. 5 is an illustration at a scale smaller than those of FIGS. 1 through 4 of a vascular prosthesis with a lateral opening implanted in an artery with a branch.

The endoprosthesis 30 illustrated in place in FIG. 5 has a lateral aperture 31. This aperture expands considerably as the prosthesis' lumen expands from its initially narrow state to the width characteristic of the in-place prosthesis. The expanded aperture allows unimpeded supply to a branch 33 of the artery 32 accommodating the endoprosthesis.

Figure 6:
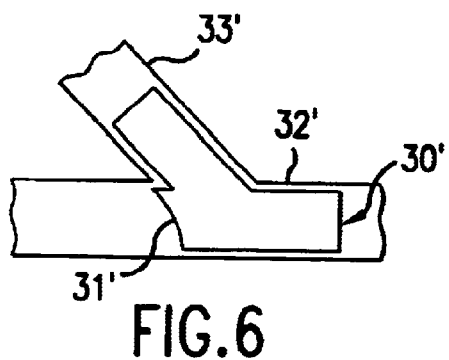
FIG. 6 is a view similar to that in FIG. 5 of a vascular prosthesis with a lateral opening that allows blood to flow through a major artery, whereas the stent itself extends along a branch.

FIG. 6 on the other hand illustrates an endoprosthesis 30' with a lateral aperture 31' that allows the blood to flow essentially unimpeded through main artery 32', whereas the stent itself extends into a subsidiary branch 33'. The subsidiary branch could just as well be a bypass, in which event the lateral aperture would be coaxial with the main branch.

Figure 7:
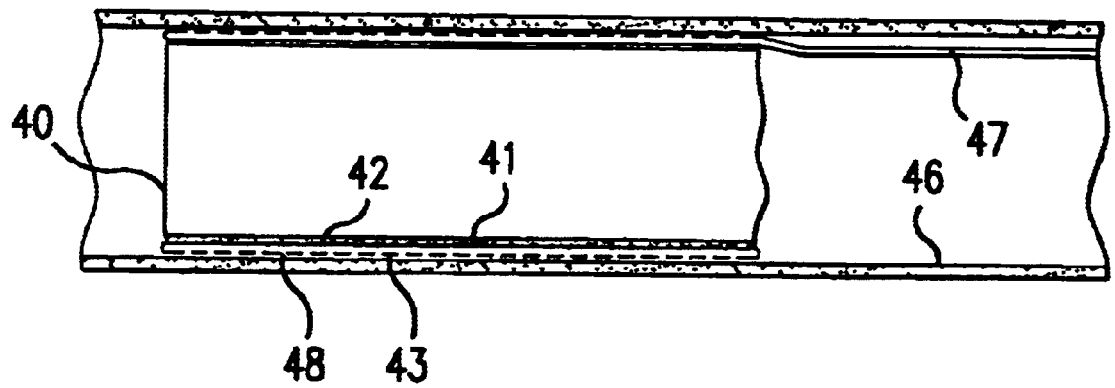

The endoprosthesis 40 in the embodiment illustrated in FIG. 7 comprises a stent enclosed in a lining 42 and 43 in the form of a double walled sleeve. The outer lining component 43 of the in-place and expanded stent rests against the inner surface 46 of the blood vessel. Inner lining component 42 rests against the stent. Between the two walls is enough room to accommodate medications, which can penetrate to inner surface 46 through openings 18 that extend through outer lining component 13. Inner lining component 12 can also have (unillustrated) openings, even more or less than outer lining component 13. A flexible tube 47 can extend through the space between lining components 42 and 43 more or less coaxial with the axial extent of endoprosthesis 40 and along the inner surface of the blood vessel, allowing a continuous supply of medication.

Flexible medicating tube 47 can also be attached to and detachable from the lining so that it can be removed once enough medication has been supplied. An appropriate plug can be provided on the lining to plug up the opening of the tube.

Figure 8:
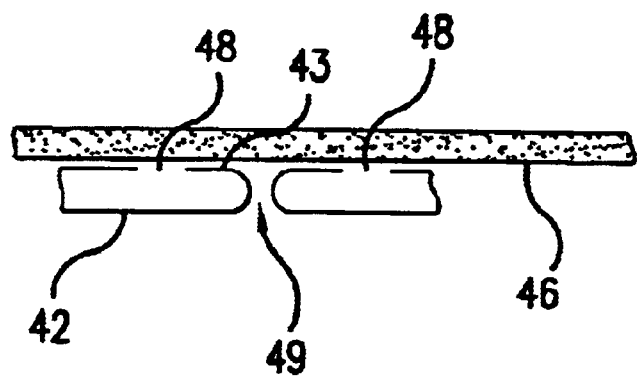
FIG. 8 is a section illustrating the openings and pores in the lining illustrated in FIG. 7.

FIG. 8 illustrates a section of the membrane-like lining with pores 49 that extend through both components in addition to openings 48 that extend only through outer lining component 43. The pores constitute radial channels of communication that allow the diffusion of metabolites between the wall and the lumen of the vessel.

A medication can be supplied long-term to the inner surface 46 of the vessel by the endoprosthesis 40 illustrated in FIGS. 7 and 8 without essentially interfering with the flow of blood. The infusions can be introduced into the flexible lining subject to slight pressure, whence they will accordingly exit also subject to only slight pressure through the openings in lining components 42 and 43. The risk of mechanical damage to the wall 46 of the vessel is accordingly negligible.

The infusions can also be administered at an appropriate and defined concentration, extensively avoiding damage to the vessel or cells.

Substances other than medications can also be introduced into the flexible lining in order to supply nutrients to the wall of the vessel. Glucose and/or such chemical buffers as bicarbonate, to obtain a pH beneficial to the treatment, can in particular be administered. Among the medications that can be administered are anti-arteriosclerotics and genetic mechanisms to regulate the vascular metabolism. Antithrombotics can be administered, preferably through the holes in the inner wall of the flexible lining, to inhibit thromboses on the inner surface.

The lining in all the embodiments specified hereinbefore by way of example can plastically deform to prevent fissuring as it expands. This feature is characteristic not only of the embodiments in the form of flexible tubes but also of stents with a non-tubular (bulk) lining.

What is claimed is:

1. An endoprosthesis comprising:
   an elongated hollow structure,
      the structure being deliverable into a body lumen of a patient for dwelling therein,
      the structure being expandable and having an initial state of decreased outer diameter during delivery relative to the outer diameter of the structure during dwelling; and
   a lining impregnated with a medication for delivery to the patient,
      the lining being continuous and connected along the structure and expandable therewith,
      the lining deforming plastically during the expansion of the hollow structure, such that the lining does not crack during expansion.

2. The endoprosthesis of claim 1 wherein the structure is in the form of a mesh of interconnected open loops forming apertures.

3. The endoprosthesis of claim 2 wherein the lining encloses the mesh covering the apertures.

4. The endoprosthesis of claim 2 wherein the lining encloses the mesh without covering the apertures.

5. The endoprosthesis of claim 1 further comprising:
   a detachable medicating tube associated with the lining.

6. The endoprosthesis of claim 1 wherein the lining includes an outer layer having pores which widen during expansion, the medication being released upon expansion of the outer layer.

7. The endoprosthesis of claim 1 wherein the lining includes an inner layer having pores which widen during expansion, the medication being released upon expansion of the inner layer.

8. The endoprosthesis of claim 1 wherein the medication includes a genetic material.

9. The endoprosthesis of claim 1 wherein the medication includes an anti-arteriosclerotic.

10. The endoprosthesis of claim 1 wherein the medication includes an antithrombotic.

11. The endoprosthesis of claim 1 wherein the medication includes a cytostatic.

12. The endoprosthesis of claim 1 wherein the medication is dissolved in the lining.

13. The endoprosthesis of claim 1 wherein the medication is encapsulated in beads impregnated in the lining.

14. The endoprosthesis of claim 1 wherein the lining is biodegradable.

15. The endoprosthesis of claim 1 wherein the lining includes pores.

16. The endoprosthesis of claim 15 wherein the lining has pores with a diameter no larger than 0.5 $\mu$m.

17. The endoprosthesis of claim 1 wherein the lining comprises more than one layer.

18. The endoprosthesis of claim 17 wherein each of the layers includes a different medication.

19. The endoprosthesis of claim 17 wherein the layers biodegrade at different rates.

20. The endoprosthesis of claim 17 wherein an inner layer biodegrades more rapidly than an outer layer.

21. The endoprosthesis of claim 17 wherein an inner layer is impregnated with a rheological substance and an outer layer is impregnated with a cytostatic.

22. The endoprosthesis of claim 1 wherein the lining has a cuff at one end.

23. The endoprosthesis of claim 1 further comprising:
   at least one medicating tube in fluid communication with the lining.

24. The endoprosthesis of claim 23 wherein the at least one medicating tube is releasably coupled to the lining.

25. The endoprosthesis of claim 23 wherein the at least one medicating tube comprises apertures of medicating tubes uniformly distributed around the lining.

26. The endoprosthesis of claim 23 wherein the at least one medicating tube is adapted to accommodate radioactive liquids.

27. The endoprosthesis of claim 1 wherein the lining is made of at least one of the following compounds: a polyacrylic or albumin cross-linked with glutaraldehyde.

28. The endoprosthesis of claim 1 wherein the lining is permeable to metabolites and oxygen.

29. The endoprosthesis of claim 1 wherein the lining has been formed around the structure by placing the structure into a mold and pouring the lining material into the mold.

30. The endoprosthesis of claim 1 wherein the lining is sized to engage the structure after the structure has expanded to more than substantially half of its final deployed size.

* * * * *